(12) United States Patent
Haiat et al.

(10) Patent No.: US 11,864,807 B2
(45) Date of Patent: Jan. 9, 2024

(54) DEVICE FOR INSERTING A SURGICAL IMPLANT

(71) Applicants: CENTRE NATIONAL DE LA RECHERCHE SCIENTIFIQUE (CNRS), Paris (FR); Université Paris XII Val de Marne, Creteil (FR)

(72) Inventors: Guillaume Haiat, Rungis (FR); Giuseppe Rosi, Paris (FR); Antoine Tijou, Créteil (FR)

(73) Assignees: CENTRE NATIONAL DE LA RECHERCHE SCIENTIFIQUE (CNRS), Paris (FR); Université Paris XII Val de Marne, Creteil (FR)

( * ) Notice: Subject to any disclaimer, the term of this patent is extended or adjusted under 35 U.S.C. 154(b) by 626 days.

(21) Appl. No.: 16/650,641

(22) PCT Filed: Sep. 27, 2018

(86) PCT No.: PCT/EP2018/076224
§ 371 (c)(1),
(2) Date: Mar. 25, 2020

(87) PCT Pub. No.: WO2019/063673
PCT Pub. Date: Apr. 4, 2019

(65) Prior Publication Data
US 2020/0246053 A1    Aug. 6, 2020

(30) Foreign Application Priority Data

Sep. 29, 2017    (FR) ..................... 1759136

(51) Int. Cl.
*A61B 17/92* (2006.01)
*A61F 2/46* (2006.01)
*A61B 17/00* (2006.01)

(52) U.S. Cl.
CPC ............ *A61B 17/92* (2013.01); *A61B 17/921* (2013.01); *A61F 2/4607* (2013.01);
(Continued)

(58) Field of Classification Search
CPC ...... A61F 2002/4666; A61F 2002/4681; A61F 2/4609; A61B 2017/00119;
(Continued)

(56) References Cited

U.S. PATENT DOCUMENTS 4,422,320 A * 12/1983 Moorby ................... G01N 3/30
73/12.09
4,479,386 A * 10/1984 Beggs ..................... G01N 19/04
73/579

(Continued)

FOREIGN PATENT DOCUMENTS

EP    2923677 A1    9/2015
FR    3019031 A1    10/2015
(Continued)

OTHER PUBLICATIONS

International Search Report issued in PCT/EP2018/076224 dated Jan. 22, 2019 (9 pages).
(Continued)

*Primary Examiner* — David W Bates
(74) *Attorney, Agent, or Firm* — Osha Bergman Watanabe & Burton LLP

(57) ABSTRACT

A device for forcibly inserting a surgical implant into a receiving bone (4), by impaction, comprising an impactor (10) which exerts an impact force on the implant and is associated with at least one sensor (12). The sensor (12) measures the deformation of the impactor (10), and provides a measurement signal representing the temporal variation of the deformation during an impact. The sensor (12) is connected to a processing unit (30) configured to calculate, on
(Continued)

the basis of the temporal variation of the deformation of the impactor (10) during the impact, an indicator representative of the level of contact between the implant and the receiving bone (4).

17 Claims, 3 Drawing Sheets

(52) U.S. Cl.
CPC ..... *A61F 2/4609* (2013.01); *A61B 2017/0011* (2013.01); *A61B 2017/00022* (2013.01); *A61B 2017/00119* (2013.01); *A61B 2017/922* (2013.01); *A61F 2002/4681* (2013.01)

(58) Field of Classification Search
CPC ...... A61B 2560/0462; A61B 2090/064; A61B 17/922; A61B 17/92; A61B 2090/032; A61B 2090/065; G01P 15/09; G01L 5/0052; G01L 5/0028; G01N 2203/0623; G01N 2203/0039; G01N 3/30
See application file for complete search history.

(56) References Cited

U.S. PATENT DOCUMENTS

| | | | | |
|---|---|---|---|---|
| 4,534,206 | A * | 8/1985 | Kiso | G01M 7/08 73/12.09 |
| 4,615,209 | A * | 10/1986 | Change, Jr. | G01N 3/30 73/12.09 |
| 4,689,985 | A * | 9/1987 | Glass, III | G01L 5/0052 73/11.01 |
| 5,025,655 | A * | 6/1991 | Umemura | G01N 3/30 73/12.09 |
| 5,079,728 | A * | 1/1992 | Adams | G01N 3/48 702/42 |
| 6,748,791 | B1 * | 6/2004 | Georgeson | G01N 29/4427 73/12.06 |
| 6,884,264 | B2 * | 4/2005 | Spiegelberg | A61F 2/30771 606/92 |
| 7,900,498 | B1 * | 3/2011 | Ratcliffe | G01N 3/30 73/12.09 |
| 11,234,825 | B2 * | 2/2022 | Johannaber | A61B 34/25 |
| 2004/0200263 | A1 * | 10/2004 | Saegusa | G01N 3/30 73/11.01 |
| 2007/0149981 | A1 * | 6/2007 | Bhattacharyya | A61F 2/4603 606/99 |
| 2008/0125671 | A1 * | 5/2008 | Meneghini | A61F 2/4657 600/553 |
| 2008/0255806 | A1 * | 10/2008 | Sambuelli | G01N 3/30 702/183 |
| 2010/0249657 | A1 * | 9/2010 | Nycz | A61B 90/06 606/53 |
| 2010/0249796 | A1 * | 9/2010 | Nycz | A61F 2/4684 600/587 |
| 2014/0165696 | A1 * | 6/2014 | Hao | G01N 3/30 73/12.09 |
| 2014/0275815 | A1 | 9/2014 | Stein et al. | |
| 2015/0282856 | A1 * | 10/2015 | Haiat | A61F 2/4609 606/100 |
| 2017/0196506 | A1 * | 7/2017 | Behzadi | A61B 7/023 |
| 2017/0196711 | A1 | 7/2017 | Behzadi | |
| 2017/0292900 | A1 * | 10/2017 | Kuo | G01L 5/0052 |
| 2017/0340456 | A1 * | 11/2017 | Behzadi | A61B 7/023 |
| 2018/0116821 | A1 * | 5/2018 | Johannaber | A61B 17/92 |
| 2019/0125293 | A1 * | 5/2019 | Behzadi | A61B 7/023 |
| 2019/0133547 | A1 * | 5/2019 | Behzadi | A61F 2/468 |
| 2020/0229858 | A1 * | 7/2020 | Haiat | A61F 2/4657 |
| 2020/0294423 | A1 * | 9/2020 | Blain | G09B 23/285 |
| 2021/0018397 | A1 * | 1/2021 | Xin | G01M 7/08 |
| 2021/0145603 | A1 * | 5/2021 | Dun | A61F 2/4603 |
| 2021/0161576 | A1 * | 6/2021 | Haiat | A61B 5/4504 |
| 2021/0244487 | A1 * | 8/2021 | Beck | G06N 3/08 |
| 2021/0361336 | A1 * | 11/2021 | Adekanmbi | A61F 2/4657 |

FOREIGN PATENT DOCUMENTS

| | | |
|---|---|---|
| JP | H06-210436 A | 8/1994 |
| JP | 2011-161581 A | 8/2011 |
| WO | 2010/111272 A1 | 9/2010 |
| WO | 2015/048908 A1 | 4/2015 |
| WO | 2016/123700 A1 | 8/2016 |

OTHER PUBLICATIONS

Written Opinion of the International Searching Authority issued in PCT/EP2018/076224 dated Jan. 22, 2019 (9 pages).
Office Action issued in the counterpart Japanese Patent Application No. 2020-539135, dated Oct. 4, 2022 (10 pages).
Office Action issued in the counterpart Chinese Patent Application No. 201880063726.6, dated Aug. 24, 2022 (12 pages).
Universal Quartz, Low-Impedance, Voltage-Mode, Force Transducer with built-in amplifier, Series 208; PCB Piezotronics; Force & Motion, 1986 (1 page).

* cited by examiner

DEVICE FOR INSERTING A SURGICAL IMPLANT

TECHNICAL FIELD

The invention relates to a device for inserting a surgical implant into a receiving bone, by impaction. This device comprises a percussion tool, or impactor, for exerting an impact force (directly or indirectly) on the surgical implant in order to forcibly insert the implant into the receiving bone.

BACKGROUND

In the present disclosure, the concept of surgical implant is not limited to surgical implants per se, but also includes surgical instruments temporarily inserted into a receiving bone. This concept covers, in particular, all orthopedic prosthesis implants intended to replace a deficient joint, in particular implants for hip, knee, shoulder, elbow, spine or ankle prostheses, and the fitting instruments used to prepare the receiving bone to receive the prosthesis.

Forcible insertion of a surgical implant into a receiving bone is often accomplished by impaction using an impactor, typically a hammer. An ancillary tool may also be used, the practitioner using the impactor to strike the ancillary tool which transmits the impaction force to the implant.

As the number of impacts increases, the implant becomes embedded in the receiving bone. The level of contact between the implant and the surrounding bone depends on this embedding. This level of contact is generally characterized by the BIC ratio, which stands for bone to implant contact ratio, which is the percentage of the surface area of the implant in contact with the bone. The further the implant is embedded in the receiving bone, the higher the BIC ratio.

The practitioner generally wishes to monitor the embedding of the implant in the bone and determine the moment at which the level of contact between the implant and the bone is optimal or, at the very least, satisfactory. The practitioner also wishes to ascertain the level of primary stability of said implant. The success of the surgical operation of inserting the implant depends simultaneously on a sufficient level of contact between the implant and the receiving bone, on the level of primary stability and on avoiding damage, in particular avoiding inducing fractures or microcracks in the receiving bone during insertion. If the implant is insufficiently inserted into the receiving bone and/or insufficiently stable, this may result in micromovements of the implant, which may require another surgical intervention.

A compromise must therefore be found between a number of impacts high enough to obtain a satisfactory level of bone-implant contact, and low enough not to risk damaging the receiving bone. However, it is difficult for the practitioner to himself reliably assess the correct number of impacts. To be specific, it is difficult for him to know precisely when to stop striking the implant with the impactor.

In this context, one aim of the invention is to propose a device making it possible to provide, during the surgical operation, reliable information on the level of contact between the implant and the receiving bone, thus enabling the practitioner to ascertain, in real time, when he should stop striking the implant with the impactor.

Patent FR 3019031 describes a device for assisting the fitting of an orthopedic implant, comprising an impactor for impacting an impact surface coupled to the implant and exerting an impact force on the implant. The impactor has a striking face for impacting the impact surface. A force sensor is secured to the striking face and converts the temporal variation of the impact force exerted into an exploitable electrical signal.

Although generally satisfactory, the device of document FR 3019031 has the drawback that the force sensor must meet several requirements. It must first have sufficient mechanical strength to be able to withstand the mechanical stresses resulting from the impact force exerted. It must also withstand high temperatures because, before a surgical operation, the impactor and its sensor must be sterilized. During sterilization, the impactor and its sensor are typically brought to high temperature, for example, by being kept for 18 minutes at 134° C. under a pressure of 2 bar in an autoclave. These requirements in terms of mechanical strength and resistance to high temperatures significantly limit the choice among commercially available sensors and the sensors meeting these requirements are generally expensive.

There is therefore a need for a new type of device which, while meeting the general objectives pursued by the invention, makes it possible to overcome, or at the very least limit, the abovementioned drawbacks.

GENERAL PRESENTATION

The invention relates to a device for forcibly inserting a surgical implant into a receiving bone, by impaction. This device comprises an impactor for impacting an impact surface coupled to said surgical implant and exerting an impact force on the implant.

The impactor is associated with at least one sensor adapted for measuring the deformation of the impactor, and for providing a measurement signal representing the temporal variation of this deformation during an impact.

The sensor (i.e. said at least one sensor) is connected to a processing unit configured to calculate, on the basis of the temporal variation of the deformation of the impactor during the impact, an indicator representative of the level of contact between the implant and the receiving bone. The electronic connection between the sensor and the processing unit may be wired or not.

The proposed solution is based on the implementation of one or more deformation sensors associated with the impactor and delivering a measurement signal, the recording and analysis of this signal making it possible to determine an indicator indicating the level of contact between the implant and the receiving bone. When several sensors are used, the signals respectively delivered by these sensors may, for example, be averaged or combined to obtain the measurement signal which will be analyzed and on the basis of which the indicator will be calculated.

Compared to the force sensor used in the prior art, the deformation sensor does not convert the impact force exerted by the impactor into an exploitable electrical signal, but converts the deformation of the impactor into an exploitable electrical signal. Consequently, the deformation sensor does not have to directly withstand the mechanical stresses resulting from the impact force exerted and the requirements for the sensor in terms of mechanical strength are lower. The choice among commercially available sensors is thus greater and the suitable deformation sensors are generally less expensive than the force sensors used in the prior art.

The proposed device makes it possible, during the surgical implant insertion operation, to inform the practitioner in real time about the level of contact reached between the implant and the receiving bone. In addition to its reduced cost, this device has the advantage of being simple to use. In particular, with this device, the practitioner's gesture during the operation can remain the same, in which case the practitioner does not have to learn new gestures and can benefit from the experience he has already acquired with conventional devices.

In addition to the features just mentioned above, the proposed device may include one or more of the following features, considered in isolation or according to technically possible combinations:

- the processing unit comprises a low-pass filter for attenuating in the measurement signal the frequencies above a threshold value of between 20% and 100% of the resonance frequency of the impactor,
- the processing unit comprises a low-pass filter for attenuating in the measurement signal the frequencies above a threshold value of between 1 kHz and 35 kHz, in particular between 5 kHz and 20 kHz,
- the impactor has a striking face for impacting the impact surface, an opposite face, opposite to the striking face, and side faces extending between the striking face and the opposite face, and said at least one sensor is secured to at least one of the side faces or to the opposite face,
- the impactor has a front face on which a protuberance is formed, the front face of this protuberance forming the striking face, and the sensor is arranged on a side face of the protuberance.

In some embodiments, the proposed indicator corresponds to the average of the deformation, calculated over a time window of programmable duration positioned on said measurement signal.

The start of said time window may coincide with the instant the measurement signal reaches its maximum amplitude. The duration of said time window may then be between 0.1 ms and 5 ms, particularly between 0.1 ms and 0.5 ms and more particularly equal to 0.25 ms. As an alternative, the start of the time window may be defined with a predetermined delay, which may vary from 0 to 5 ms, relative to the instant the measurement signal reaches its maximum amplitude.

For example, the indicator IN1 is calculated as follows:

$$IN1 = \frac{1}{A_1 \cdot (t_2 - t_1)} \int_{t_1}^{t_2} A(t) \cdot dt$$

where:

$A(t)$ corresponds to the amplitude of said measurement signal at the instant t;

$A_1$ corresponds to the maximum amplitude of said measurement signal; and $t_1$ and $t_2$ correspond respectively to the start and end instants of the time window.

As an alternative, said indicator is determined by said processing means as being the duration of impact measured on the basis of the measurement signal (i.e. the temporal variation of the deformation during an impact). This duration corresponds to the duration (ti2−ti1) separating an instant ti1 corresponding to the start of the impact and an instant ti2 corresponding to the end of the impact. For example, the instant ti2 of end of impact may be chosen as the instant the amplitude of the deformation falls below a predefined limit value.

In other embodiments, the indicator corresponds to the duration of a time window, the start of this time window being defined with respect to an instant corresponding to the first peak of maximum amplitude of the measurement signal and the end of this time window being defined with respect to an instant corresponding to the second peak of maximum amplitude of the measurement signal.

All these indicators have been shown to be representative of the level of contact between the implant and the receiving bone and to constitute reliable indicators.

As a general rule, as the number of impacts increases, the level of contact between the implant and the receiving bone first increases and then tends to stabilize. When the level of implant-bone contact becomes stable, it is generally considered to be sufficient. The proposed indicator, representative of the level of contact, adopts a similar behavior and tends, as the number of impacts increases, to first increase/decrease and then to stabilize around a stationary value higher/lower than a threshold value. The values of the above examples of indicators thus decrease as the number of impacts increases, until they reach a substantially stable plateau.

It is therefore possible to derive from the behavior of the indicator a condition for emitting an alert signal (e.g. a light, a sound, a vibration, etc.). The practitioner, alerted by this signal, then knows that he must stop impacting the implant, the level of contact between the implant and the bone being considered to be optimal or, in any case, sufficient. Thus, in some embodiments, the device comprises an alert system connected to the processing unit and interacting with the latter so as to emit an alert signal when the indicator converges to a stationary value during successive impacts, or when the indicator exceeds a predetermined threshold value. This threshold value can be determined experimentally during tests, or can be determined by calculation. For example, tests can be carried out on corpses, the threshold value chosen being the value of the indicator from which there is a sufficient level of contact between the implant and the receiving bone.

In some embodiments, the impactor is a hammer, or equivalent, and comprises a gripping shaft topped by a striking head. In particular, the impactor may have substantially the same shape and the same weight as impactors commonly used to date. Thus, experienced practitioners are immediately able to handle the impactor correctly.

It will be noted that the impact surface may be directly coupled to the implant, in the sense that it may be one of the surfaces of the implant, or may be indirectly coupled to the implant, in the sense that it may be a surface of an instrument, or ancillary tool, itself coming into contact with the implant. In the latter case, the impactor exerts the impact force on the implant via the ancillary tool. In other words, the impact force is exerted on the ancillary tool and transmitted by the latter to the implant.

In some embodiments, the device comprises an ancillary tool having a rear end forming said impact surface and a front end adapted for cooperating with the implant, the impactor exerting the impact force on the implant via the ancillary tool.

The front end of the ancillary tool may cooperate with the implant by simple contact. Alternatively, the front end of the ancillary tool may be mechanically attached to the orthopedic implant in a removable manner, for example by screwing. Attaching the ancillary tool to the implant generally provides a better measurement signal. The ancillary tool is removable such that it may easily be detached from the implant once the latter is in position.

The present disclosure also relates to an assembly comprising a device as described above and a surgical implant, in particular a femoral stem or an acetabular cup.

The invention also relates to a method for forcibly inserting a surgical implant into a receiving bone, by impaction, wherein:

a device as described above is provided, an impact force is exerted on the implant with the impactor, by impacting an impact surface coupled to the implant, so as to insert the implant, the indicator is calculated to get an idea of the level of contact between the implant and the receiving bone.

In some modes of implementation, the indicator may be calculated one or more times, at the end of insertion of the implant, to verify correct implantation of the implant.

As an alternative, the indicator may be calculated during successive impacts and impacting of the impact surface is stopped when the indicator converges to a stationary value during successive impacts, or when the indicator exceeds a predetermined threshold value.

The surgical implant may be, but is not necessarily, an acetabular cup. In this case, the cup is impacted with the impactor so as to forcibly insert the cup into a cavity in the iliac bone. The indicator may be calculated at the end of insertion, to check that the cup has been correctly put in place.

The advantages of such a method stem from the advantages of the device used.

The aforementioned features and advantages, as well as others, will emerge on reading the following detailed description of exemplary embodiments of the proposed device. This detailed description refers to the attached drawings.

BRIEF DESCRIPTION OF THE DRAWINGS

The attached drawings are schematic and are not to scale; their primary purpose is to illustrate the principles of the invention.

(FIG. 1 shows an example of a device 1 for forcibly inserting a surgical implant into a receiving bone, by impaction. In this example, the implant is an implant for a prosthesis, in particular for a hip prosthesis. The vast majority of hip prostheses have in common a first part fixed in the femur and a second part fixed in the pelvis. The first part comprises a femoral stem intended to be forcibly inserted into the medullary canal of the femur and a prosthetic head consisting of a spherical piece, mounted on the femoral stem and replacing the neck of the femur. The second part comprises a prosthetic acetabulum intended to be inserted into the acetabular cavity located on the lateral face of the iliac bone of the pelvis, to replace the articular part of the pelvis. The prosthetic acetabulum may comprise an acetabular cup, which is an approximately hemispherical piece, generally made of metal, inserted into the acetabular cavity and in which is placed an insert with which the prosthetic head is articulated.

Figure 1:
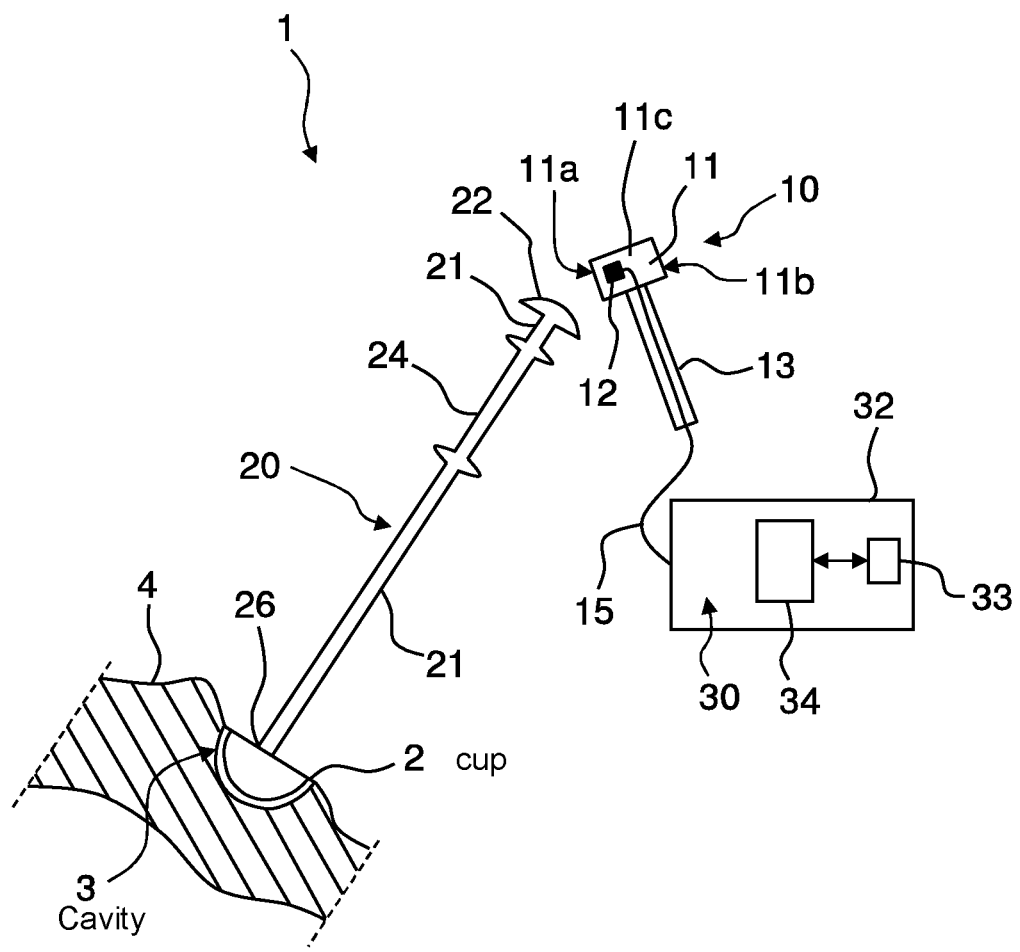
FIG. 1 schematically shows a device for inserting a surgical implant, comprising an impactor having a deformation sensor.

The implant of FIG. 1 is an acetabular cup 2. This cup 2 is intended to be inserted gradually by impaction into the acetabular cavity 3 of the iliac bone 4 of the pelvis of a patient, the cavity 3 having been previously prepared by the practitioner to receive the cup 2. The insertion of the cup 2 into the cavity 3 is accomplished by impaction using an impactor 10, typically a hammer. An ancillary tool 20 may also be used. In this case, the practitioner strikes the ancillary tool 20 with the impactor 10 and the ancillary tool 20 transmits the impact force to the cup 2. As the number of impact increases, the cup 2 becomes embedded in the cavity 3.

The ancillary tool 20 is made of a rigid rod 21, at the rear end of which is rigidly secured a knob having a domed surface, forming an impact surface 22. Along the length of the rod 21, from its rear end to its front end, the rod 21 comprises said knob, a portion forming a handle 24, a front portion and a head 26 for gripping the cup 2. The front and the rear are defined in this case with respect to the direction of forward travel of the ancillary tool 20 during impaction.

The device 1 also comprises a percussion tool or impactor 10, such as a hammer or equivalent, comprising a gripping shaft 13 topped by a striking head 11. The head 11 has a striking face 11a for impacting the impact surface 22 of the ancillary tool 20, an opposite face 11b, opposite to the striking face 11a, and side faces 11c extending between the striking face 11a and the opposite face 11b.

When the practitioner wishes to embed the cup 2 in the bone 4, he grasps the ancillary tool 20 with one hand, by the handle 24, and the gripping shaft 13 of the impactor 10 with the other hand. He then strikes the impact surface 22 of the ancillary tool 20 with the striking face 11a of the impactor 10. The impact force generated by the impactor 10 is transmitted to the cup 2 via the ancillary tool 20.

According to the invention, the impactor 10 is equipped with one or more deformation sensors 12. This or these sensors 12 are for detecting the deformation of the impactor 10, more precisely of the striking head 11, during each impact and converting this deformation into an exploitable electrical signal.

In the example of FIG. 1, the impactor 10 is equipped with a deformation sensor 12 positioned on one of the side faces 11c of the striking head 11. In this case, the sensor 12 is positioned on the side face 11c extending substantially parallel to the direction of the axis of the gripping shaft 13. More specifically, seen from the side (as in FIG. 1), the sensor 12 is secured to the front part of the side face 11c, between the striking face 11a and the axis of the gripping shaft 13. This particular arrangement of the sensor 12 on the striking head 11 makes it possible to optimize the deformations measured and, therefore, to obtain a measurement signal that carries better information and is more easily exploitable. However, in general, the deformation sensor or sensors 12 may be positioned on any face of the impactor 10 except the striking face 11a (i.e. on the side faces 11c or on the opposite face 11b).

Figure 3:
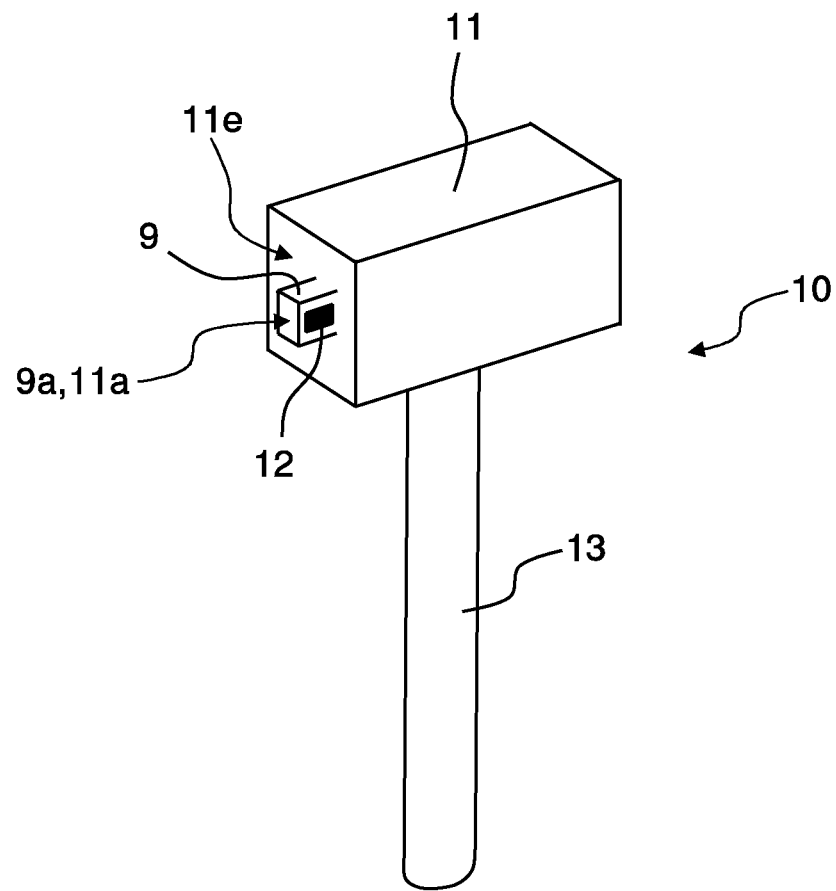

Alternatively, as shown in FIG. 3, the impactor 10 has a front face 11e on which a protuberance 9 is formed. The front face 9a of this protuberance 9 forms the striking face 11a of the impactor 10, and the sensor 12 is secured to a side face of the protuberance 9, i.e. to a face of the protuberance 9 extending between the impact face 11a and the front face 11e of the impactor. This particular arrangement of the sensor 12 on the striking head 11 of the impactor 10 makes it possible to optimize the deformations measured and to avoid, at least in part, the resonance frequencies specific to the impactor 10. It thus makes it possible to obtain a measurement signal that carries better information and is more easily exploitable.

The deformation sensor 12 is secured to the striking head 11, for example by adhesive bonding or any other suitable securing means, such that the deformation of the striking head 11 causes the deformation of the sensor 12. The sensor 12 is, for example, a gauge sensor comprising an elastic measurement element, the deformation of which is first converted into a variation in the electrical resistance of the gauge, to then generate an electrical output signal. Alternatively, it may be a piezoelectric sensor based on the piezoelectric properties of a material (e.g. quartz or synthetic ceramics) which generates an electrical charge when it deforms. The sensor 12 is secured to the striking head 11 of the impactor 10, for example by adhesive bonding or any other suitable securing means, such that the deformation of the striking head 11 causes the deformation of the sensor. By way of example, the deformation sensor 12 may be a sensor measuring 20×20 mm, sold under the brand PI and the reference PIC255, and be adhesively bonded to the impactor 10 with epoxy adhesive capable of withstanding the temperatures reached in an autoclave.

The device also includes a processing unit 30 connected to the sensor 12 and configured to evaluate the degree of insertion of the cup 2 into the receiving bone 4, on the basis of the measurement signals delivered by the sensor 12. This processing unit 30 comprises, for example, a microcontroller 34. The processing unit 30 may be housed in an external housing 32. As an alternative, the processing unit 30 may be integrated in the impactor 10. According to another alternative (not shown), the processing unit 30 may be formed of separate elements such as a microcomputer connected to a data acquisition module itself connected to the sensor 12.

The connection between the sensor 12 and the processing unit 30 is, in the example of FIG. 1, wired by means of a cable 15. As an alternative, the measurement signals supplied by the sensor 12 may be transmitted by means of a wireless connection, in which case the sensor 12 is equipped with an antenna or equivalent.

Figure 2:
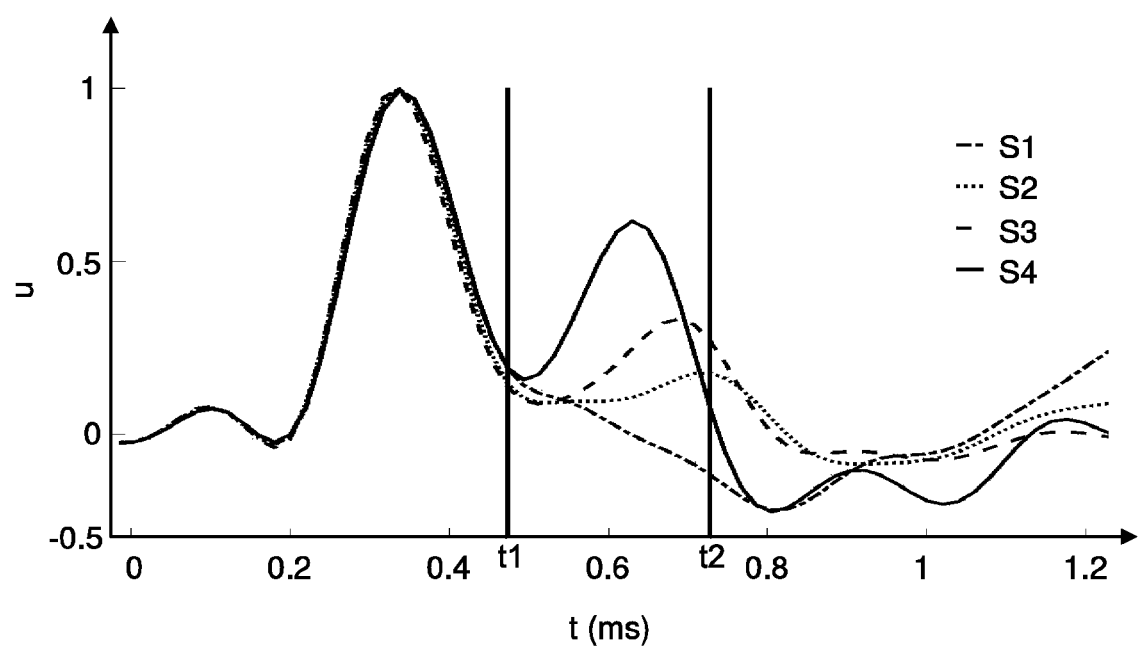
FIG. 2 is a graph showing examples of signals obtained using the deformation sensor of FIG. 1, and FIG. 3 schematically shows another example of an impactor.

During each impact performed by the practitioner on the cup 2 by means of the impactor 10, via the ancillary tool 20, the sensor 12 measures the deformation of the striking head 11 of the impactor 10 and supplies a measurement signal representing the temporal variation of this deformation during the impact. It is considered that the impact begins from the instant the impactor 10 and the implant come into contact, directly or indirectly (i.e. via the ancillary tool 20), and lasts for a certain period of time after this instant. In any event, this period of time is less than 50 ms. Examples of signals supplied by the sensor 12 are shown in FIG. 2 and described below.

The inventors decided to take look at such a measurement signal and established that this signal carried information on the level of contact between the cup 2 and the bone 4. In particular, the inventors succeeded in determining, on the basis of the measurement signal collected, an indicator representative of the level of contact between the bone 4 and the cup 2, as explained below.

In an attempt to explain the link between the measurement signal collected and the level of bone-implant contact, the following explanation can be offered. The impactor 10 exerts on the cup 2, via the ancillary tool 20, an impact force which is the source of modes of vibration in the whole system made up of the impactor 10, the ancillary tool 20, the cup 2 and the bone 4 when these elements are all in contact during impact. These modes of vibration essentially depend on the modes of vibration of the bone-implant system (i.e. of the bone-cup system) which in turn depend on the level of contact between the implant and the bone. In essence, the greater the level of bone-implant contact, the more rigid the bone-implant system and the higher the resonance frequencies of the modes of vibration.

In some embodiments, the processing unit 30 comprises a low-pass filter for attenuating in the measurement signal the frequencies above a threshold value. This threshold value is in particular chosen to attenuate in the signal the influence of the resonance of the impactor itself. The resonance frequency of the impactor is constant for a given impactor and significantly higher than the frequencies of the signals carrying information on the bone-implant system. In particular, for the insertion of the cup 2 of FIG. 1, the impactor 10 may have a resonance frequency of around 20 kHz or more, while the frequencies of the useful signal supplied by the sensor 12 are generally less than 5 kHz. The threshold value may thus be chosen at between 5 kHz and 20 kHz.

The low-pass filter therefore makes it possible to attenuate in the measurement signal the frequencies close to and above the resonance frequency of the impactor 10, which are characteristic of the modes of vibration specific to the impactor 10 and which do not carry information on the level of contact between the implant and the bone, while retaining the lower frequencies, which are characteristic of the modes of vibration of the whole system made up of the impactor 10, the ancillary tool 20, the cup 2 and bone 4, and which carry information on the level of bone-cup contact. The quality of the measurement signal in terms of useful information is thereby improved and the signal is more easily exploitable.

FIG. 2 is a graph showing examples of signals obtained using the deformation sensor 12 for different levels of bone-implant contact. These signals were obtained during four tests aimed at revealing the correlation between the proposed indicator and the level of contact between the implant and the bone. These four tests were carried out using four samples of bovine bone obtained from a butcher's shop. For each sample, a cavity was made under the same conditions and with the same equipment as during a surgical operation. The cup 2 was then positioned above the cavity and impact forces were applied as is done in the clinic. For each sample, the cup 2 was pushed in until it was fully embedded in the bone. Once the cup was fully embedded, the cup 2 was moderately struck with the impactor 10 of FIG. 1. This moderate impact was not intended to modify the position of the cup 2 in the bone, but to calculate the indicator on the basis of the measurement signal emitted by the deformation sensor 12. Once the indicator was calculated, the cup 2 was torn from the bone by exerting on the cup a pulling force along the axis of the cup 2. This pulling force, or tearing force, reflects the level of contact between the implant and the receiving bone: the greater the level of bone-implant contact, the more difficult it is to tear the implant from the bone, and the higher the tearing force.

In the graph of FIG. 2, the time t in milliseconds (ms) is plotted on the X-axis, and the normalized voltage u of the electrical signal supplied by the sensor 12 during the aforementioned four tests is plotted on the Y-axis. This voltage is directly proportional to the deformation of the striking head 11 measured by the sensor 12. The four signals are referenced S1 to S4. These signals were normalized and filtered.

For each signal, the indicator IN1 was calculated as follows:

$$IN1 = \frac{1}{A_1 \cdot (t_2 - t_1)} \int_{t_1}^{t_2} A(t) \cdot dt$$

where:

A(t) corresponds to the amplitude of the measurement signal at the instant t;

$A_1$ corresponds to the maximum amplitude of said measurement signal; and $t_1$ and $t_2$ correspond respectively to the start and end instants of a time window of programmable duration positioned on said measurement signal.

In this case, in this example, the instants $t_1$ and $t_2$ are identified in FIG. 2 and were determined by implementing an optimization process.

The table below gives, for each signal S1 to S4, the values of the calculated indicator and of the tearing force measured, in Newtons.

|    | Indicator IN1 | Tearing force (N) |
|----|---------------|-------------------|
| S1 | 0.1           | 13.6              |
| S2 | 0.26          | 50.8              |
| S3 | 0.48          | 95.4              |
| S4 | 0.94          | 179               |

These results illustrate the correlation that exists between the proposed indicator and the tearing force, and therefore between the proposed indicator and the level of bone-implant contact. This indicator may therefore be used to assess the level of bone-implant contact.

With reference to FIG. 1, the device 10 may include an alert system 33 for emitting an alert signal (for example, an audio, visual and/or tactile signal). The alert system 33 is connected to the processing unit 30 and interacts with the latter to alert the practitioner when the level of contact between the cup 2 and the bone is deemed sufficient on the basis of the indicator IN1, i.e., for example, as soon as the indicator IN1 drops below the threshold value S1 or when this indicator IN1 tends to become stabilized. Consequently, the practitioner has reliable information in real time indicating that he has reached a sufficient level of bone-implant contact. He concludes that he can stop impacting the cup 2, which reduces the risk of damaging the bone 4, in particular of inducing a fracture or microcracks in the bone.

The example which has just been described, concerning the insertion of a cup 2 into an iliac bone 4, is given by way of non-limiting illustration, and a person skilled in the art could easily use the indicator proposed by the inventors with other types of implants, without departing from the scope of the invention. In other words, the cup 2 and the bone 4 are only examples of a surgical implant and a receiving bone, respectively, within the meaning of the invention.

In particular, the proposed device may be used for implants for a hip prosthesis other than an acetabular cup (e.g. for a femoral stem), implants for a knee, shoulder, spine, ankle, etc. prosthesis and, more generally, any type of surgical implant requiring forcible insertion into a receiving bone by impaction. It may also be used for the insertion of surgical instruments temporarily inserted into the body of a patient and, for example, for the insertion of a surgical rasp such as a femoral rasp for a hip prosthesis. Femoral rasps are designed to be forcibly inserted, by impaction, into the medullary canal in order to prepare this canal to receive the femoral stem. These rasps are impacted directly by an impactor, with or without the intermediary of an ancillary tool. If no ancillary tool is used, the impact surface is then constituted by a surface located at the rear end of a gripping part of the rasp.

Lastly, the various features of the embodiments or examples described in the present disclosure may be considered in isolation or be combined with one another. When they are combined, these features may be as described above or otherwise, the invention not being limited to the specific combinations described above. In particular, unless otherwise specified or technically incompatible, a feature described in relation to one embodiment or example may be applied in a similar manner to another embodiment or example.

The invention claimed is:

1. A device for forcibly inserting a surgical implant into a receiving bone, by impaction, comprising:
    an impactor for impacting an impact surface coupled to the implant and exerting an impact force on the implant,
    at least one deformation sensor associated with the impactor, and
    a processing unit connected to the at least one deformation sensor,
    wherein:
    the at least one deformation sensor is adapted for measuring the deformation of the impactor induced by the impact force, and for providing a measurement signal representing the temporal variation of this deformation during an impact,
    the processing unit is configured to calculate, on the basis of the temporal variation of the deformation of the impactor during the impact, an indicator representative of the level of contact between the implant and the receiving bone,
    the impactor has a striking face for impacting the impact surface, an opposite face, opposite to the striking face, and side faces extending between the striking face and the opposite face, and
    the at least one deformation sensor is bonded to at least one face among the side faces and the opposite face, so that the deformation of the at least one face causes the deformation of the at least one deformation sensor.

2. The device according to claim 1, wherein the processing unit comprises a low-pass filter for attenuating in the measurement signal the frequencies above a threshold value of between 20% and 100% of the resonance frequency of the impactor.

3. The device according to claim 1, wherein the processing unit comprises a low-pass filter for attenuating in the measurement signal the frequencies above a threshold value of between 1 kHz and 35 kHz, in particular between 5 kHz and 20 kHz.

4. The device according to claim 1, wherein the impactor has a front face on which a protuberance is formed, the front face of the protuberance forming the striking face, and wherein the at least one deformation sensor is arranged on a side face of the protuberance.

5. The device according to claim 1, wherein the indicator (IN1) corresponds to the average of the deformation, calculated over a time window of programmable duration positioned on the measurement signal.

6. The device according to claim 5, wherein the indicator IN1 is calculated as follows:

$$IN1 = \frac{1}{A_1 \cdot (t_2 - t_1)} \int_{t_1}^{t_2} A(t) \cdot dt$$

where:
- A(t) corresponds to the amplitude of the measurement signal at instant t;
- $A_1$ corresponds to the maximum amplitude of the measurement signal; and
- $t_1$ and $t_2$ correspond respectively to the start and end instants of the time window.

7. The device according to claim 1, wherein the indicator corresponds to the duration of a time window, the start of the time window being defined with respect to an instant corresponding to the first peak of maximum amplitude of the measurement signal and the end of the time window being defined with respect to an instant corresponding to the second peak of maximum amplitude of the measurement signal.

8. The device according to claim 1, further comprising an alert system connected to the processing unit and interacting with the latter so as to emit an alert signal when the indicator converges to a stationary value during successive impacts, or when the indicator exceeds a predetermined threshold value.

9. The device according to claim 1, further comprising an ancillary tool having a rear end forming the impact surface and a front end adapted for cooperating with the implant, the impactor exerting the impact force on the implant via the ancillary tool.

10. The device according to claim 1, wherein the impactor is a hammer, or equivalent, and comprises a gripping shaft topped by a striking head, and wherein the at least one deformation sensor is secured to the striking head such that the deformation of the striking head causes the deformation of the at least one deformation sensor.

11. The device according to claim 10, wherein the striking head has a plurality of faces forming the striking face, the opposite face, and the side faces, the side faces extending substantially parallel to the direction of an axis of the gripping shaft.

12. An assembly comprising a device according to claim 1 and a surgical implant.

13. A method for forcibly inserting a surgical implant into a receiving bone, by impaction, wherein:
- a device according to claim 1 and a surgical implant are provided,
- an impact force is exerted on the implant with the impactor, by impacting an impact surface coupled to the implant, so as to insert the implant,
- the indicator is calculated to get an idea of the level of contact between the implant and the receiving bone.

14. The device according to claim 10, wherein the at least one deformation sensor is positioned on a front part of the side face extending substantially parallel to the direction of an axis of the gripping shaft, between the striking face and the axis of the gripping shaft.

15. The assembly according to claim 12, wherein the surgical implant is a femoral stem or an acetabular cup.

16. The device according to claim 1, wherein the at least one deformation sensor comprises an elastic measurement element.

17. The device according to claim 1, wherein the at least one deformation sensor is a piezoelectric sensor based on a material that generates an electrical charge when the material deforms.

* * * * *